United States Patent [19]

Arndt

[11] Patent Number: 4,923,297
[45] Date of Patent: May 8, 1990

[54] OPTICAL ALIGNMENT SYSTEM

[75] Inventor: Joseph H. Arndt, Portland, Oreg.

[73] Assignee: Eyedentify, Inc., Portland, Oreg.

[21] Appl. No.: 877,509

[22] Filed: Jun. 23, 1986

[51] Int. Cl.$^5$ ............................................. A61B 3/02
[52] U.S. Cl. ..................................... 351/208; 351/223
[58] Field of Search ............... 351/207, 208, 223, 237, 351/243; 350/171, 173; 356/399

[56] References Cited

U.S. PATENT DOCUMENTS

| | | |
|---|---|---|
| 1,834,017 | 3/1931 | Carbonara . |
| 2,232,177 | 2/1941 | Ide . |
| 3,600,098 | 8/1971 | Mohrman ............................ 351/208 |
| 3,871,772 | 3/1975 | Munnerlyn et al. ................ 351/208 |
| 4,272,191 | 9/1981 | Bergkvist ............................ 356/399 |
| 4,322,137 | 3/1982 | Nohda . |

Primary Examiner—Rodney B. Bovernick
Assistant Examiner—J. Patrick Ryan
Attorney, Agent, or Firm—Eugene D. Farley

[57] ABSTRACT

A quasi-reticle for an optical device, generated by enhanced multiple reflections. The reticle comprises fixation target generative means operative to generate a line of ghost images or other multiple fixation targets spaced along the optical axis of the optical device, whereby to enable the viewer by aligning his line of sight with the line of multiple fixation targets to position his eye properly with respect to the optical axis of the optical device.

14 Claims, 3 Drawing Sheets

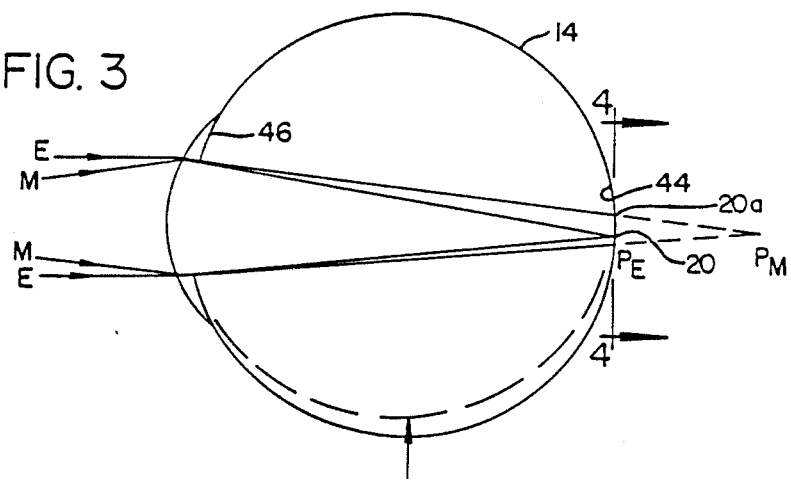
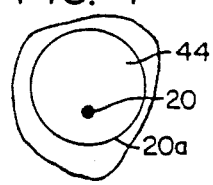
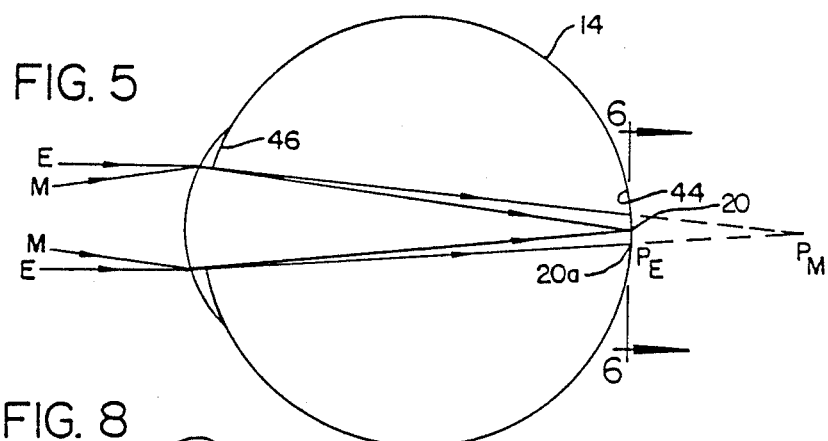
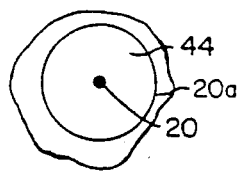
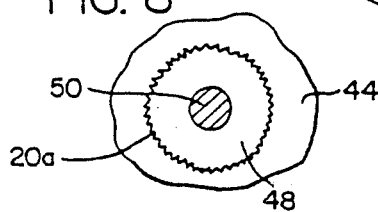
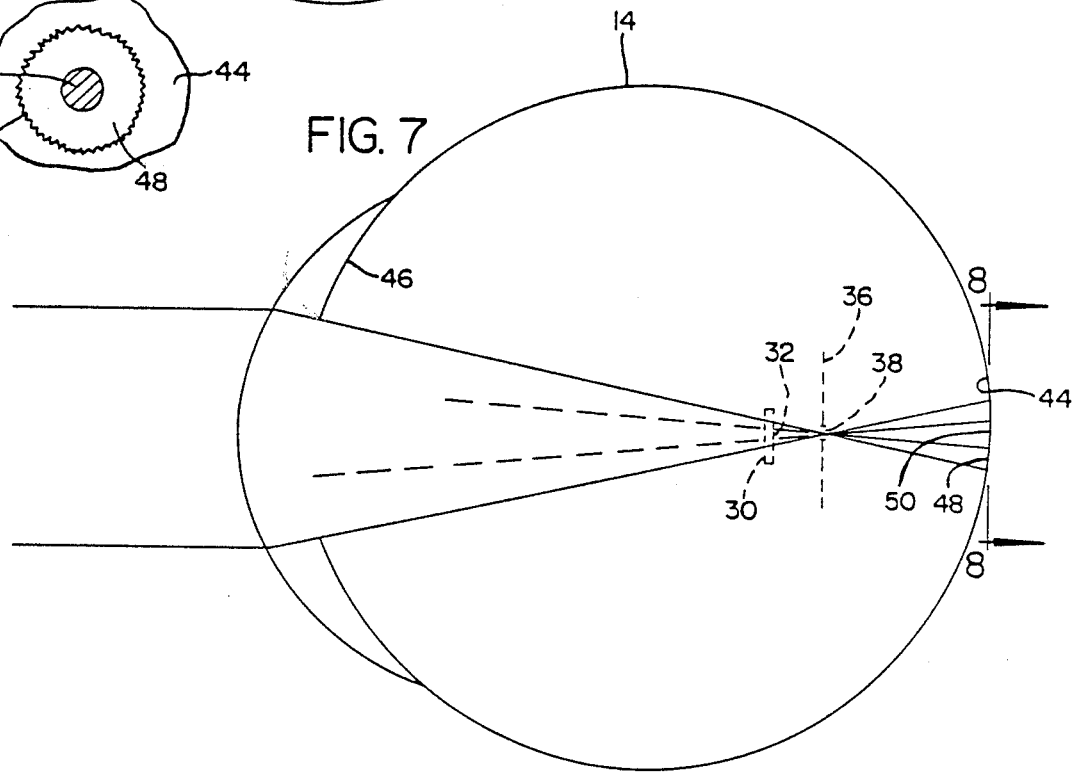

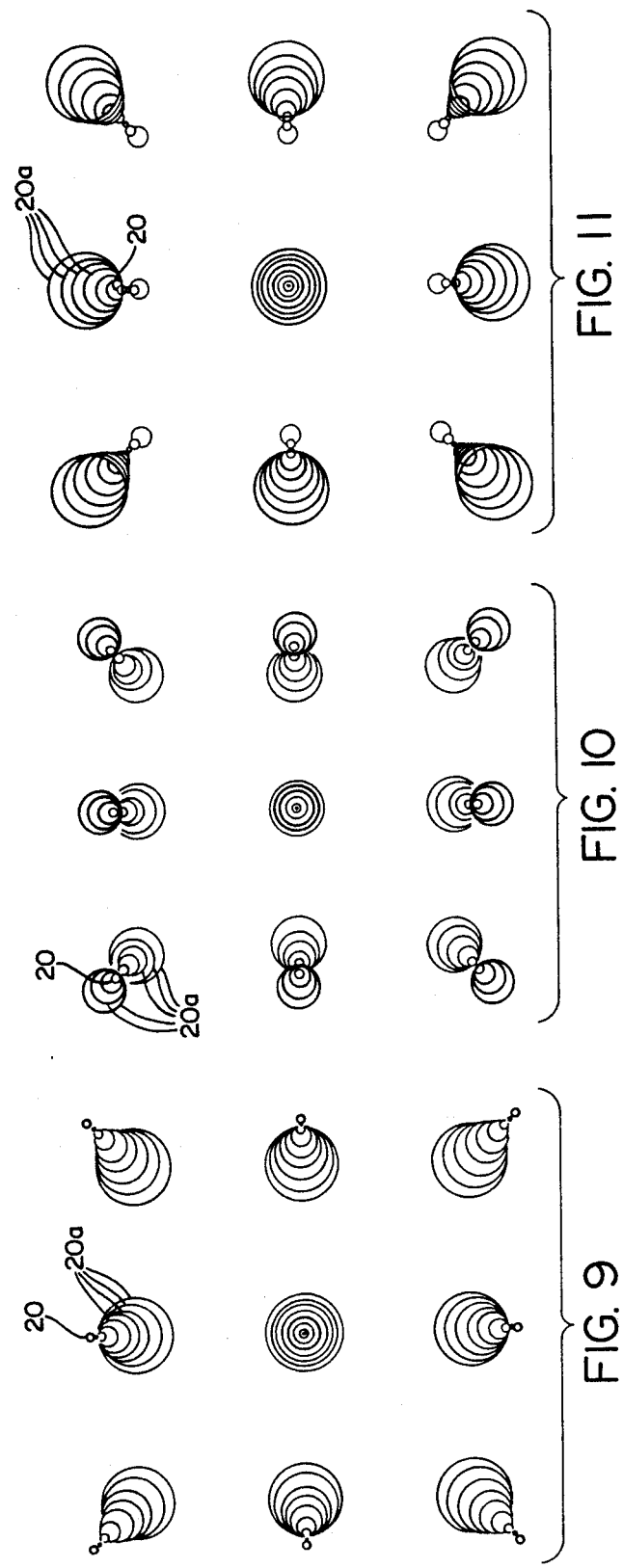

OPTICAL ALIGNMENT SYSTEM

BACKGROUND AND GENERAL STATEMENT OF THE INVENTION

This invention pertains to optical alignment systems. It pertains particularly to line of sight aligning devices for use with optical instruments having viewing openings requiring precise alignment with the line of sight of the viewer.

In the field of optics there are many optical instruments which, for their proper and accurate use, require precise alignment of the line of sight of the viewer with a viewing opening in the instrument. This is the case, for example, in Hill, U.S. Pat. No. 4,109,237 and Hill, U.S. Pat. No. 4,393,366 both of which pertain to apparatus and method for identifying individuals through their retinal vasculature patterns. The apparatus employed directs a beam of light into the eye of the subject and reads the retinal vasculature pattern from the reflected light. The resulting information then is used for identification of the subject.

In this sequence, it is imperative that the line of sight of the subject be located precisely with respect to the analyzing instrument in order to obtain reproduceable results.

Without mechanical assistance, precise location inherently is difficult of achievement. It is difficult for a viewer, unassisted, to align his eye precisely with the viewing opening of an instrument.

It accordingly is the general purpose of the present invention to provide an aligning device for use with optical instruments having viewing openings requiring precise alignment of the line of sight of the viewer.

It is a further object of the present invention to provide an optical aligning device which is simple, easy to use, usable in conjunction with a wide variety of optical instruments, and highly accurate.

Further objects of the present invention are the provision of an optical aligning device the application of which is obvious intuitively even to the technologically naive, being readily understood and easily mastered with minimum training time.

Other important objects of the present invention are the provision of an optical alignment device the use of which is independent of the viewer's refractive error, which does not require focusing, which controls or compensates for four of the six degrees of freedom of positioning of the viewer's head/eye (translation of the head up and down, and side to side; and angular rotation of the eye up and down, and side to side); which is monochromatic so that there is no color blindness problem; and which does not require use of special lenses or eyeglasses.

The foregoing and other objects of this invention are achieved by an optical aligning device which, broadly considered, comprises, in combination with the device, fixation target generating means operative to generate a line of multiple fixation targets spaced along the optical axis of the device, whereby to enable the viewer, by aligning his line of sight with the line of multiple fixation targets, to position his eye precisely on the optical axis of the device.

The fixation target generating means broadly comprises multiple light reflection (ghost image) generating means which in turn comprises a light emitting diode or other light source directed against a double coated mirror which is so constructed as to develop the multiple ghost images spaced along the optical axis of the device. By positioning his eye so that the ghost images are directly in line, the viewer accordingly is assured that his eye, or line of sight, is located precisely on the optical axis of the optical instrument.

THE DRAWINGS

In the drawings:

FIG. 1 is a schematic view in side elevation illustrating the optical alignment device of the invention and its manner of use, FIG. 2 is a schematic fragmentary view in side elevation of a light emitting diode and a double reflecting mirror which are preferred components of the presently described optical aligning device, FIGS. 3–11 inclusive are schematic views illustrating the manner of application of the herein described optical alignment device.

DESCRIPTION OF A SPECIFIC EMBODIMENT OF THE INVENTION

The optical alignment device of the present invention replaces such prior art alignment devices as a reticle illuminated through a pinhole artificial pupil (to reduce the effects of refractive error) and surrounding annulus (to indicate decentering).

As indicated above, the device basically comprises fixation target generative means operative to generate a line of multiple fixation targets spaced along the optical axis of the device, enabling the viewer, by aligning his line of sight with the line of multiple fixation targets, to position his eye precisely on the optical axis of the device.

The line of multiple fixation targets thus could comprise a line of physically spaced transparent plates, each having scribed or etched on its surface a dot or other mark, the dots being aligned with each other and lying on the optical axis of the instrument. However, it is preferred to employ fixation target generating means comprising a multiple light reflection, or ghost image, generator, the light reflections comprising the fixation targets.

Figure 1:
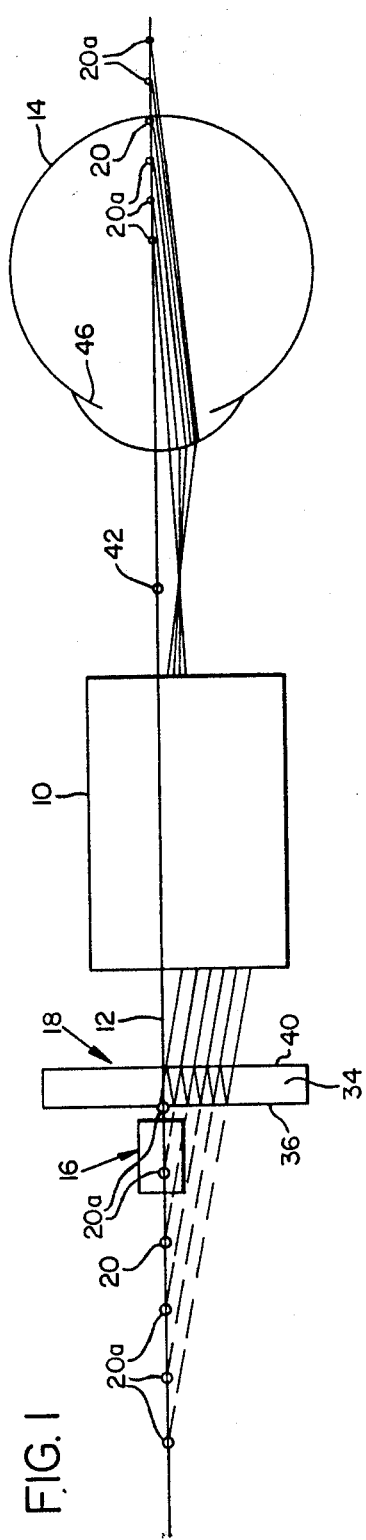

An illustrative system for achieving this purpose is illustrated schematically in FIG. 1.

In FIG. 1, the optical instrument 10 having an optical axis 12 is shown in relation to the eye 14 of the viewer. The aligning device comprises a light source indicated generally at 16 and a doubly reflecting mirror indicated generally at 18. The light source and mirror coact to produce the desired line of multiple fixation target images 20, 20a spaced along the optical axis of the instrument.

Figure 2:
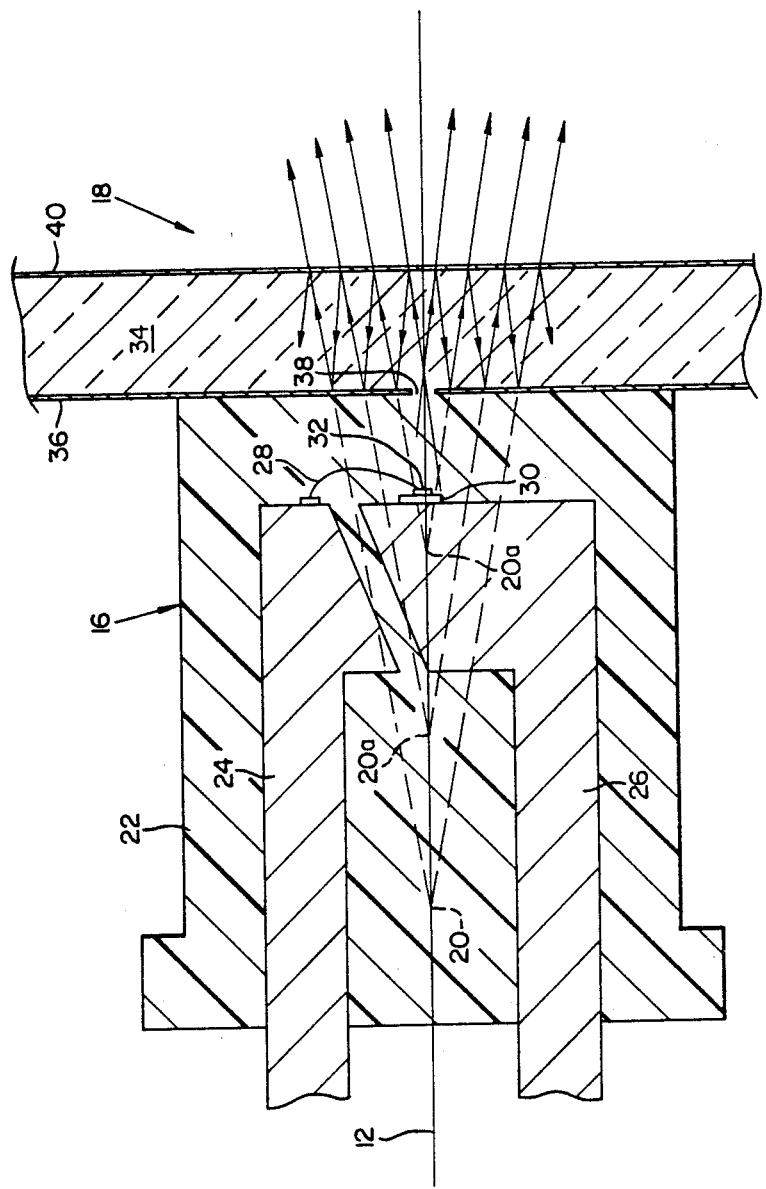

Although various types of light sources such as incandescent lights, fluorescent lights, etc. can be employed for the purposes of invention, it is preferred to employ a conventional light emitting diode (LED), the construction of which is illustrated particularly in FIG. 2.

A support 22 supports electrodes 24, 26. The electrodes are interconnected by means of wire 28 which energizes the luminescent chip 30 in the usual manner. Wire 28 is electrically connected to luminous chip 30 by means of a non-luminous bead or pad of solder 32.

This plays an important part in the present invention, since the presence of the centrally located solder pad on the face of the luminous chip results in a light source with a central obscuration, rather than a uniform disk.

The light emitting diode is positioned on the optical axis 12 of instrument 10, with solder pad 32 precisely positioned thereon. Accordingly, in the beam emitted by the diode there will be a void located precisely on the optical axis. The importance of this will appear hereinafter.

The beam of light emitted by the light emitting diode is directed against doubly reflective mirror 18. The construction and manner of functioning of this mirror is illustrated in detail in FIG. 2.

The mirror body 34 comprises a sheet of glass, clear plastic, or other transparent substance having substantially parallel surfaces. The face or front surface is nearer the LED and the rear surface is on the opposite side. The front surface is coated with an opaque fully reflective mirror coating 36. This may comprise a silver, aluminum, or other metallic mirror coating. Located centrally, on the optical axis of the instrument, is a pinhole 38. This lies directly opposite solder pad 32 on the LED.

The rear surface of double reflective mirror 18 has a coating 40 which is semitransparent, commonly used as a beam-splitter. It is composed preferably of dielectric, non-absorbing, coating materials such as magnesium fluoride and silicon oxide. While the light reflection/transmission ratio of the coating is variable, it should be relatively high, i.e. from about 50/50% to about 95/5%, preferably from about 75/25% to about 90/10%.

The action of the semitransparent mirror thus is such as to reflect most of the light back towards the mirror and to transmit only a small portion to eventually reach the viewer's eye. The reflected portion is distributed among ghost images of the pinhole, or dots, represented at 20, 20a in the drawings. The higher the product of the reflectivities of the mirror coating 36 and the beam splitter coating 40, the more ghost images will be visible.

Other design parameters are the optical thickness of the ghost image generating element (which determines the spacing between images), the parallelism of the glass plate (which governs whether the images lie along a line or the arc of a circle), and the geometry of the light source, i.e. the LED chip, and its distance behind the pinhole. The chip must be close enough so that the pupil of the viewer's eye, and not the edge of the chip, is the limiting aperture stop., but not so close that the dark solder pad prevents any light from reaching the viewer's retina.

As illustrated in FIG. 1, between the ghost image generating means and the viewer are one or more optical elements which determine where the primary image of the pinhole and its ghost images appear to the viewer. The optical system is designed to distribute the images uniformly along the line of sight when the image is in the desired position and fixation direction.

Where object and image are uniformly spaced points along the optic axis, the design process is simplified if parallel rays are considered, one from each object point. If the image points are also uniformly spaced. these rays will also be parallel inside the eye. Such rays must all pass through a common point 42 in front of the eye known as the first focal position. According to the "Military Standardization Handbook Optical Design" (MIL-HDBK-141) the first focal position is 15.59 mm anterior to the cornea of the standard eye. The optical system design requirements then are reduced to causing the parallel rays from the ghost image generating element to pass through that point.

The manner of generation of a defocussed image or dot is explained in FIGS. 3-6.

As shown in FIGS. 5 and 6, rays marked M would come to a focus at $P_M$, except that they hit the retina 44 first, in a circular blur rather than in a point. The rays marked E come to a focus at $P_E$ coincident with the retina, and form a small focused dot 20, centered in the circle if the eye is correctly positioned.

As shown in FIGS. 3 and 4, when the eye is displaced in the upward direction the patterns formed by nearby objects are displaced more than the more distant ones, and the pattern is asymmetric, resulting in the small focussed dot 20 being decentered with respect to the defocussed circular blur 20a.

The manner of generation and appearance of a single defocussed dot is shown in greater detail in FIGS. 7 and 8.

The dot acts as a pinhole camera, imaging the light source, defined by the iris 46 of the viewer's eye as its outside limit and by the LED chip's solder pad as its inside feature.

As shown in FIG. 8, this generates a ring of light 48 surrounding a dark center 50.

In general, the defocussed image is annular, with the outer edge jagged, as is the inner edge of the yiewer's iris. Irregular shaped pupils, astigmatism, etc., may produce less regular patterns; nevertheless it still is possible for the viewer to align his line of sight with the optical axis of the instrument.

The manner in which this is done, independently of optical aberrations due to any optical defects which may characterize the eye of the viewer, is further illustrated in FIGS. 9-11.

In these figures, FIG. 9 illustrates the effect when viewed by a viewer having a condition of myopia; FIG. 10, by a viewer having normal vision; and FIG. 11, by a viewer having a condition of hyperopia. In these views, the images or dots 20 which are in focus are represented by small circles; those which are out of focus 20a by large circles.

When the optical system is used by a myopic viewer, the situation is as illustrated in FIG. 9. The peripheral views of that figure indicate viewer head position in which the line of sight is not aligned with the optical axis of the instrument, in the directions indicated by the axes of the concentric circles. When the head position is such that the line of sight is exactly on the optical axis of the instrument, the condition illustrated in the central figure obtains: i.e., that of a bulls-eye.

As is evident from a consideration of FIGS. 10 and 11, this same bulls-eye end result obtains when the viewer's eye is normal, and also when it is hyperopic, no matter which dot is in focus.

In summary, the image alignment system of my invention is a simple but effective device to provide for the viewer of an optical system a series of visible dots that are distributed along the line of sight such that, regardless of the viewer's spherical refractive error (corrected or not), at least one of the dots will be sufficiently in focus to provide a well-defined fixation target, without the need for adjustable focusing mechanisms.

Furthermore, nearby dots, although slightly out of focus, are sufficiently well-defined to provide visible parallax effects to enable the viewer to move in the plane normal to the line of sight to that position in which the dots lie along the line of sight and the observed pattern of defocused dots is concentric and/or symmetric about the in-focus dot.

According to the Military Standardization Handbook, cited above, 98% of the population has refractive errors not exceeding ±4 diopters. In a representative implementation of the presently described device, the nearest dot is in sharp focus for an extremely near-sighted viewer with a refractive error of minus eight diopters. There is no limit to the most distant dots except that they become increasingly fainter, with usable dots extending beyond what would be in sharp focus for a far-sighted viewer with a refractive error of plus twenty diopters.

In the use of a light source with a dark center, such as the above described solder pad on an LED chip, there result out-of-focus dots also having dark centers. This permits the smaller images of the more-in-focus dots to be more easily seen and fixated on. The overall pattern takes on the appearance of a "bulls-eye" when the eye is correctly positioned, with the fixation point at the center of the concentric circles. The viewer's procedure is obvious intuitively, even to the technologically naive., readily understood and easily mastered, and effective in producing an accurate result.

Having thus described in detail a preferred embodiment of the present invention, it will be apparent to those skilled in the art that various physical changes could be made in the device described herein without altering the inventive concepts and principles embodied. The present embodiment is therefore to be considered in all respects as illustrative and not restrictive, the scope of the invention being indicated by the appended claims rather than by the foregoing description. All changes which come within the meaning and range of equivalency of the claims are therefore to be embraced therein.

I claim:

1. In combination: an optical device having an optical axis with which the line of sight of a viewer's eye is to be precisely aligned; and means for producing a plurality of visible fixation targets spaced apart along said optical axis, whereby a viewer positions his/her eye in a plane normal to said viewer's line of sigh to align said line of sight precisely with the optical axis of the optical device, the means for producing a plurality of visible fixation targets comprising a light source positioned substantially on the optical axis of the optical device and, in spaced relation thereto, double coated mirror means in which the coatings are on opposite parallel surfaces, said light source and mirror means forming multiple ghost image generating means, the primary image and its ghost images comprising the visible fixation targets, the double coated mirror means comprising a sheet of light-transmitting material having substantially parallel surfaces, the front surface being coated with an opaque reflective mirror coating material rendering it reflective and being provided with a pinhole located substantially on the optical axis of the optical device, and the rear surface being coated with a semi-transparent reflective mirror coating material imparting to it a light reflection/transmission ratio of from about 50/50% to about 95/5%.

2. The combination of claim 1 wherein the light reflection/ transmission ratio is from about 75/25% to about 90/10%.

3. The combination of claim 1 wherein the opaque coating material comprises metallic silver, aluminum, or other reflective metal.

4. The combination of claim 1 wherein the semitransparent coating material comprises a dielectric, substantially non-light-absorbing, beamsplitter-type coating material.

5. The combination of claim 4 wherein the semitransparent coating material comprises magnesium fluoride.

6. The combination of claim 4 wherein the semitransparent coating material comprises silicon oxide.

7. The combination of claim 1 wherein the opaque reflective mirror coating material comprises metallic aluminum and the semitransparent coating material comprises a dielectric, substantially non-absorbing, beamsplitter-type reflective coating material.

8. In an optical device having an optical axis with which the line of sight of a viewer's eye is to be precisely aligned, the method of positioning the eye of a viewer precisely on said optical axis, comprising projecting a plurality of visible ghost image fixation targets at spaced intervals along said optical axis, and moving the eye of the viewer in a plane normal to the viewer's line of sight to align said ghost image fixation targets on the line of sight of the viewer, wherein the fixation targets are provided by arranging a source of light so that when the plurality of ghost image fixation targets are aligned on the line of sight of the viewer, they are seen by the viewer as a plurality of concentric circles.

9. In combination: an optical device having an optical axis with which the line of sight of a viewer's eye is to be precisely aligned; means for producing a plurality of visible ghost image fixation targets spaced apart along said optical axis, whereby the viewer positions his/her eye in a plane normal to said viewer's line of sight to align said line of sight precisely with the optical axis of the optical device.

10. The combination of claim 9 wherein the plurality of visible ghost image fixation targets comprises a source of light, and light reflecting means arranged to reflect light from said source to a plurality of positions spaced apart along the optical axis of the optical device.

11. The combination of claim 10 wherein the source of light provides a spot of light with a dark center, whereby the plurality of visible ghost image fixation targets are light spots with dark centers located on the optical axis of the optical device.

12. The combination of claim 10 wherein the source of light comprises a light emitting diode including a luminescent chip and a non-luminous pad at the center of the chip disposed on the optical axis of the optical device, whereby the plurality of visible ghost image fixation targets are light spots with dark centers located on the optical axis of the optical device.

13. The combination of claim 9 wherein the means for producing a plurality of visible ghost image fixation targets comprises a light source positioned substantially on the optical axis of the optical device and, in spaced relation thereto, double coated mirror means in which the coatings are on opposite parallel surfaces, said light source and mirror means forming multiple ghost image generating means, the primary image and its ghost image comprising the visible fixation targets.

14. In combination: an optical device having an optical axis with which the line of sight of a viewer's eye is to be precisely aligned; and means for producing a plurality of visible ghost image fixation targets spaced apart along said optical axis, whereby a viewer positions his/her eye in a plane normal to said viewer's line of sight to align said line of sight precisely with the optical axis of the optical device, the means for producing a plurality of visible ghost image fixation targets comprising a light source located substantially on the optical axis of the device and including a luminescent chip having a non-luminous center generating a dark centered ring of light, and double coated mirror means comprising a sheet of light-transmissive material having substantially parallel surfaces, the face surface being coated with an opaque reflective mirror coating material rendering it reflective, and being provided with a pinhole located substantially on the optical axis of the optical device, and the rear surface being coated with a semi-transparent reflective mirror coating material of high light reflection/transmission ratio.

* * * * *